United States Patent [19]

Bartmann et al.

[11] 4,282,223

[45] Aug. 4, 1981

[54] ISOQUINOLINE DERIVATIVES, PROCESSES FOR THEIR MANUFACTURE AND THEIR USE FOR THE MANUFACTURE OF MEDICAMENTS

[75] Inventors: Wilhelm Bartmann; Elmar Konz, both of Bad Soden am Taunus; Hansjörg Kruse, Kelkheim, all of Fed. Rep. of Germany; Harry M. Geyer, Flemington, N.J.

[73] Assignee: Hoechst Aktiengesellschaft, Frankfurt am Main, Fed. Rep. of Germany

[21] Appl. No.: 76,862

[22] Filed: Sep. 19, 1979

Related U.S. Application Data

[63] Continuation-in-part of Ser. No. 20,411, Mar. 14, 1979, abandoned.

[30] Foreign Application Priority Data

Mar. 16, 1978 [DE] Fed. Rep. of Germany ....... 2811312

[51] Int. Cl.$^3$ .................. A61K 31/47; A61K 31/495; C07D 401/04

[52] U.S. Cl. ............................. 424/250; 260/244.4; 424/248.4; 424/258; 544/128; 544/295; 544/363; 546/90; 546/143; 542/413; 542/439; 542/471

[58] Field of Search ............... 544/363, 128; 546/143, 546/90; 424/250, 258

[56] References Cited

U.S. PATENT DOCUMENTS 3,975,524   8/1976   Nickl et al. ........................... 544/59

*Primary Examiner*—Paul M. Coughlan, Jr.
*Attorney, Agent, or Firm*—Curtis, Morris & Safford

[57] ABSTRACT

Isoquinolines of the formula

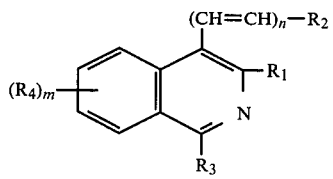

of which representative compounds are such as 3-N-methylpiperazino-1-phenyl-isoquinoline-4-aldehyde, 3-N-methylpiperazino-1-(2-fluorophenyl)-isoquinoline-4-aldehyde, or 3-N-[3-(4-fluoro-benzoyl)-propyl]-piperazino-1-phenyl-isoquinoline-4-aldehyde and medicaments containing the isoquinolines which are useful as antidepressants.

14 Claims, No Drawings

ISOQUINOLINE DERIVATIVES, PROCESSES FOR THEIR MANUFACTURE AND THEIR USE FOR THE MANUFACTURE OF MEDICAMENTS

This application is a continuation-in-part-application of U.S. patent application Ser. No. 020,411, filed Mar. 14, 1979, now abandoned.

The invention relates to isoquinolines which have basic substituents in the 3-position and possess valuable antidepressive properties.

3-Amino-4-phenyl-isoquinoline derivatives which have an action on the central nervous system are described in German Offenlegungsschrift No. 2,030,675 and 1-amino-isoquinolines which have a fungicidal and rodenticidal action are described in German Offenlegungsschrift No. 2,243,789.

The invention therefore relates to isoquinolines of the formula I

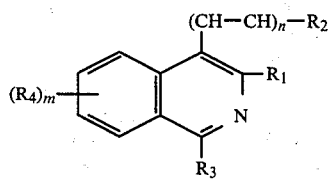

in which m denotes one or two, n denotes nought or one, $R_1$ denotes an amino group of the formula

in which $R_5$ and $R_6$ are identical or different and denote hydrogen or a straight-chain or branched, saturated or unsaturated alkyl radical with 1 to 8 carbon atoms, it being possible for the alkyl radicals also to be substituted by hydroxyl, $C_1$-$C_4$-alkoxy or an amino group of the formula

in which $R_7$ and $R_8$ are identical or different and represent hydrogen or a straight-chain or branched alkyl radical with 1 to 6 carbon atoms, or together with the nitrogen atom represent a heterocyclic ring with up to 7 carbon atoms, and the alkyl radicals $R_5$ and $R_6$, together with the nitrogen atom, can also form a 5-membered to 8-membered ring, and the heterocyclic ring can be substituted on one carbon atom by a $C_1$-$C_6$-alkyl, $C_1$-$C_4$-alkoxy, hydroxyl, carboxyl or $C_1$-$C_4$-alkoxycarbonyl group, and in the said ring one of the carbon atoms can be replaced by an oxygen, sulfur or nitrogen atom and the latter can be substituted by hydrogen, thienyl, furyl, pyridyl or formyl group, a $C_3$-$C_8$-alkenyloxycarbonyl or $C_3$-$C_8$-alkynyloxycarbonyl group, a $C_1$-$C_6$-alkoxycarbonyl group which is optionally substituted by hydroxyl or $C_1$-$C_4$-alkoxy groups, or a phenyl radical, which can be substituted by up to three $C_1$-$C_4$-alkyl, $C_1$-$C_4$-alkoxy, methylenedioxy, hydroxyl, nitro or amino groups or halogen, and the hydrogen atom on the nitrogen can, furthermore, be replaced by the radical —$COR_9$, in which $R_9$ denotes a thienyl, furyl or pyridyl radical or a phenyl radical which is optionally substituted as indicated above, or denotes a $C_1$-$C_6$-alkyl group, which in turn can be substituted by hydroxyl or a $C_1$-$C_4$-alkoxy, $C_1$-$C_6$-dialkylamino, ethylenedioxy or dimethylenedioxy group or a phenyl radical which is optionally substituted as indicated above; $R_2$ denotes a carboxyl, cyano, formyl or hydroxymethyl group, an alkoxymethyl group with 1 to 6 carbon atoms, an aminoalkyl group of the formula

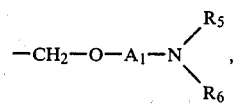

in which $A_1$ represents a straight-chain or branched $C_2$-$C_6$-alkylene group, which can be substituted by hydroxyl or $C_1$-$C_4$-alkoxy groups, and in which $R_5$ and $R_6$ are as defined above, an acyloxymethyl group of the formula —$CH_2$—O—CO—$R_{10}$, in which $R_{10}$ is a $C_1$-$C_6$-alkyl radical or a phenyl radical, which optionally can be substituted as indicated above, an aminomethyl group of the formula

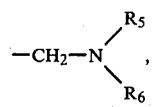

in which $R_5$ and $R_6$ are as defined above, a carboxamide group of the formula

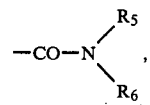

in which $R_5$ and $R_6$ are as defined above, or a carboxylic acid ester group of the formula

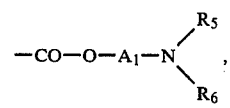

in which $A_1$, $R_5$ and $R_6$ are as defined above; $R_3$ denotes a phenyl radical, which optionally is monosubstituted or disubstituted by halogen, hydroxyl, nitro, amino or an amino group with two to eighteen carbon atoms which is substituted by one or two aliphatic, cycloaliphatic or aromatic hydrocarbon radicals and in which the nitrogen atom can also be incorporated in a heterocyclic ring, or an acylamino, alkyl or alkoxy group, each with one to six carbon atoms, a benzyloxy group or a trifluoromethyl group, or denotes a pyridyl or thienyl radical; and $R_4$ denotes hydrogen, halogen, hydroxyl, an alkyl or alkoxy group with one to six carbon atoms, or a nitro, amino, benzyloxy or methylenedioxy or ethylenedioxy group, and also their physiologically acceptable salts, processes for the manufacture of the compounds, pharmaceutical formulations and the use of the compounds.

In particular, the invention includes compounds in which $R_1$ is an amino group of the formula

in which $R_5$ and $R_6$ are identical or different and represent hydrogen or a straight-chain or branched saturated or unsaturated alkyl radical with 1 to 4 carbon atoms, and the alkyl radicals, together with the nitrogen atom, can also form a 5-membered to 7-membered ring, in which one of the carbon atoms can be replaced by an oxygen, sulfur or nitrogen atom and the latter can be substituted by hydrogen, the thienyl, furyl, pyridyl or formyl group, a $C_1$–$C_4$-alkoxycarbonyl group, which is optionally substituted by hydroxyl or $C_1$–$C_4$-alkoxy groups, the phenyl radical, which can be monosubstituted or polysubstituted by $C_1$–$C_4$-alkyl, $C_1$–$C_4$-alkoxy, methylenedioxy, hydroxyl, nitro or amino groups or halogen, and in which the hydrogen atom on the nitrogen can furthermore be replaced by the radical —$COR_9$, in which $R_9$ denotes a thienyl, furyl or pyridyl radical or a phenyl radical which is optionally substituted as indicated above, or by a $C_1$–$C_4$-alkyl group, which, in turn, can be substituted by hydroxyl, $C_1$–$C_4$-alkoxy, $C_1$–$C_4$-dialkylamino or a phenyl radical which is optionally substituted as indicated above, and in which, furthermore, if $R_5$ is hydrogen or $C_1$–$C_4$-alkyl, $R_6$ denotes an aminoalkyl radical of the formula

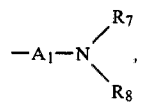

in which $A_1$, $R_7$ and $R_8$ are as defined above. The preferred substituents for $R_2$ are a carboxyl, cyano, formyl or hydroxymethyl group or an alkoxymethyl group with 1 to 4 carbon atoms or an aminoalkyl radical of the formula

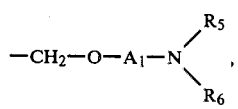

in which $A_1$, $R_5$ and $R_6$ are as defined above, or a methylamino group of the formula

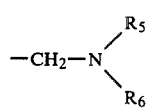

in which $R_5$ and $R_6$ are as defined above, whilst the preferred substituents for $R_3$ are a phenyl ring, which is optionally monosubstituted or disubstituted by halogen, nitro, an alkyl or alkoxy group with 1 to 4 carbon atoms or an amino group, and for $R_4$ are hydrogen, halogen, hydroxyl, nitro, amino or an alkyl or alkoxy group with 1 to 4 carbon atoms.

Compounds of very particular interest are those in which n is nought and $R_1$ denotes an amino radical of the formula

in which the alkyl radicals $R_5$ and $R_6$ together with the nitrogen atom form a 5-membered to 7-membered ring, in which one of the carbon atoms can be replaced by a N or O atom, especially the pyrrolidino, piperidino, hexamethyleneimino, morpholino, 4-hydroxypiperidino or 4-carbethoxypiperidino radical and the 1-piperazinyl radical

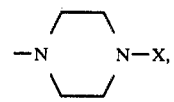

in which X denotes hydrogen, $C_1$–$C_4$-alkyl, β-hydroxyethyl, 3,4-methylenedioxybenzyl, phenyl, phenyl substituted by methoxy, chlorine, nitro or amino, 3,4,5-trimethoxybenzoyl, 3,4-methylenedioxybenzoyl, 2-furoyl, 2-thienoyl or $C_1$–$C_3$-alkoxycarbonyl, it being possible for the alkyl radical in the latter to be substituted by OH or methoxy and ethoxy, or, if $R_5$ is hydrogen or $C_1$–$C_4$-alkyl, $R_6$ represents an aminoalkyl radical of the formula

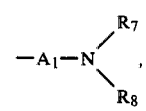

in which $A_1$, $R_7$ and $R_8$ are as defined above. Particularly important radicals as $R_2$ are the carboxyl, cyano, formyl or hydroxymethyl group, as $R_3$ are the phenyl radical, which is optionally monosubstituted or disubstituted by halogen or hydroxyl, nitro, amino or methoxy groups, and as $R_4$ are hydrogen, halogen, hydroxyl or methoxy groups, preferably in the 6-position and/or 7-position. The invention also relates to processes for the manufacture of these compounds and to pharmaceutical formulations of these compounds.

The process for the manufacture of the compounds of the formula I comprises ($a_1$) reacting compounds of the general formula II

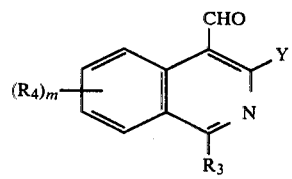

in which Y denotes chlorine or bromine and $R_3$, $R_4$ and m are as defined for formula I, with an amine of the formula

in which $R_5$ and $R_6$ are as defined for formula I, to give the compounds, according to the invention, of the formula I, in which n is nought and $R_2$ represents a formyl group, it being possible to convert these compounds, if desired, to compounds of the formula I in which n is 1 by reaction with compounds of the formula IIIa or IIIb

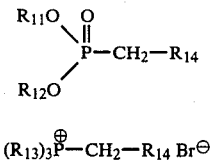   IIIa

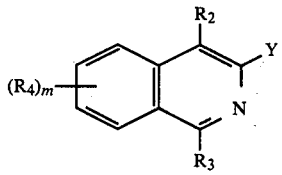   IIIb in which $R_{11}$, $R_{12}$ and $R_{13}$ denote a $C_1$-$C_4$-alkyl group or the phenyl radical and $R_{14}$ is preferably a nitrile, acetal, thioacetal or carboxylic acid ester group, (a₂) reacting compounds of the formula IV

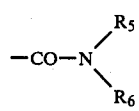   IV in which Y denotes chlorine or bromine, $R_2$ denotes a cyano group or a carboxamide group of the formula

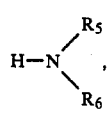

and $R_3$, $R_4$, $R_5$, $R_6$ and m are as defined for formula I, with an amine of the formula

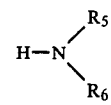

in which $R_5$ and $R_6$ are as defined for formula I, to give the compounds, according to the invention, of the formula I, (b) oxidizing compounds of the formula V

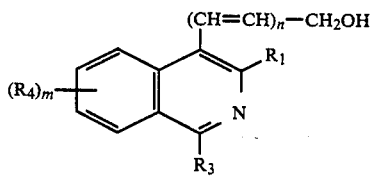   V in which $R_1$, $R_3$, $R_4$, n and m are as defined for formula I, to compounds of the formula I in which $R_2$ is a formyl group, (c) oxidizing compounds of the formula VI

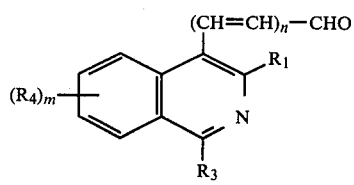   VI in which $R_1$, $R_3$, $R_4$, m and n are as defined for formula I, to compounds of the formula I in which $R_2$ is a carboxyl group, it being possible, if desired, to convert these compounds to compounds of the formula I ..., by reaction with an amine

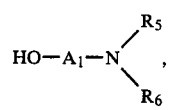

or with an alcohol of the formula

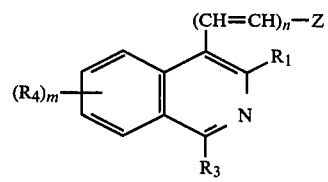

in which $R_5$, $R_6$ and $A_1$ are as defined for formula I, (d) reducing compounds of the formula VI to compounds of the formula I in which $R_2$ is a hydroxymethyl group, (e) reducing compounds of the formula VII

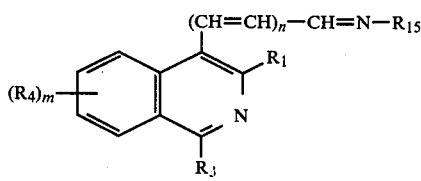   VII in which Z denotes a nitrile, carboxyl or halogenocarboxyl group or an alkylcarboxyl group with 1 to 7 carbon atoms and $R_1$, $R_3$, $R_4$, m and n are as defined for formula I, to compounds of the formula I in which $R_2$ is a formyl group, (f) reducing compounds of the formula VIII

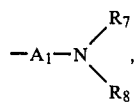   VIII in which $R_1$, $R_3$, $R_4$, m and n are as defined for formula I, to compounds of the formula I in which $R_2$ represents a methyleneamino group of the formula —$CH_2$—NH—$R_{15}$ and $R_{15}$ is to be the radical in which $A_1$, $R_7$ and $R_8$ are as defined for formula I, (g) reacting compounds of the formula IX

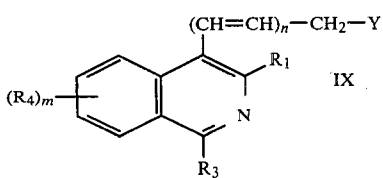

in which Y is chlorine, bromine or hydroxyl and $R_1$, $R_3$, $R_4$, m and n are as defined for formula I, with an amine of the formula

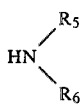

or an alcohol of the formula

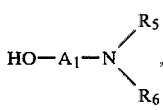

in which $A_1$, $R_5$ and $R_6$ are as defined for formula I, or an acid halide, (h) converting compounds of the formula X

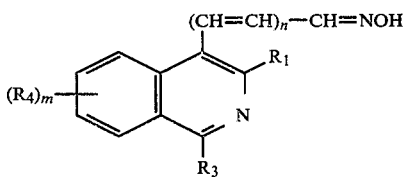

in which $R_1$, $R_3$, $R_4$, m and n are as defined for formula I, by means of dehydrating agents to compounds of the formula I in which $R_2$ is a nitrile group, (i) reacting compounds of the formula XI

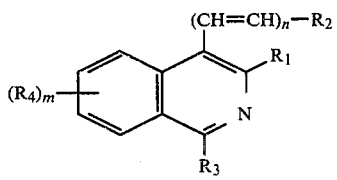

in which $R_1$ to $R_4$, m and n are as defined for formula I, with the proviso that at least one of the two radicals $R_1$ and $R_2$ contains a secondary amino group, with an alkylating agent of the formula $Y—R_{16}$, in which Y denotes chlorine or bromine and $R_{16}$ denotes a straight-chain or branched $C_1$-$C_6$-alkyl radical, which can be substituted by hydroxyl, $C_1$-$C_4$-alkoxy, $C_1$-$C_4$-dialkylamino, ethylenedioxy, trimethylenedioxy or the group

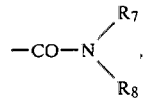

in which $R_7$ and $R_8$ are as defined for formula I, or by optionally substituted phenyl, or denotes a $C_3$-$C_8$-alkenyl or $C_3$-$C_8$-alkynyl radical, or with a chloroformic acid ester of the formula $Cl—CO_2(C_1$-$C_4)alkyl$, in which the alkyl radicals carry hydroxyl or $C_1$-$C_4$-alkoxy groups, or with a compound of the formula $Cl—COR_9$, in which $R_9$ is as defined for formula I, (j) if $R_3$ in a compound of the formula I in which $R_1$, $R_2$, $R_4$, m and n are as defined for formula I, represents the phenyl ring, subsequently substituting this phenyl ring, or (k) so changing a radical $R_4$ or substituents which may be present in the 1-position on the phenyl ring that further compounds of the general formula I are formed.

With procedure ($a_1$) or ($a_2$), at least twice the equivalent amount of amine is added since one mole of amine is used to bind the hydrogen halide split off; however, it is sometimes advantageous to use an up to 15-fold excess of the amine, in order to accelerate the reaction. If the reaction is carried out using equimolar amounts of amine, tertiary amines, such as triethylamine, pyridine or potassium carbonate can be added as acid acceptors.

If solvents are used for the reaction, these can be inert, anhydrous organic solvents, such as dioxane, 1,2-dimethoxyethane, diethylene glycol dimethyl ether, diethylene glycol dibutyl ether, benzene, toluene, xylene, chlorobenzene, dichlorobenzene, trichlorobenzene, N,N-dimethylformamide, dimethylsulfoxide or hexamethylphosphoric acid triamide. The reaction is in general carried out at a temperature between 50° and 220° C. and is preferably carried out at between 80° and 180° C. The reaction of the aldehydes with the compounds IIIa or IIIb can be carried out under the conditions customary for the Wittig or Horner reaction. Thus, for example, the reaction of the phosphonates III a can be carried out in an ether at room temperature. Preferred ethers which can be used are diethyl ether, tetrahydrofuran and dimethoxyethane. The phosphonate can be employed in an equimolar amount or in excess. Usually, the reaction has ended after 3 to 24 hours at temperatures between 10° and 50° C. Details regarding the way in which this reaction is carried out are given in J. Amer. Chem. Soc. 83, 1,733 (1961). Details on the way in which the Wittig reaction is carried out are given in J. org. Chem. 28, 1,128 (1963).

The starting compounds II for process (a) can be manufactured according to U.S. patent application Ser. No. 020.410, which was filed on Mar. 14, 1979, for example by reacting compounds of the formula IIa

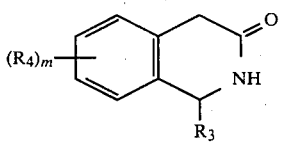

(IIa)

in which $R_3$, $R_4$ and m are as defined for formula I, with a Vilsmeier adduct of an acid amide and an acid chloride to give compounds of the formula IIb

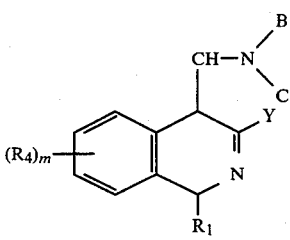

(IIb)

in which Y is chlorine or bromine and B and C denote alkyl or cycloalkyl with one to six carbon atoms or phenyl, and then oxidizing these compounds to compounds of the formula II.

In process (b), the compounds V are oxidized by known methods, for example with manganese dioxide. Oxidation reactions of this type are known (compare, for example, "Compendium of Organic Synthetic Methods", publishers John Wiley & Sons, Inc. (1971) pages 146–147, 150–152).

In process (c), the compounds VI are oxidized by known methods, for example with manganese dioxide or potassium permanganate. Oxidation reactions of this type also are known (compare "Compendium of Organic Synthetic Methods", publishers John Wiley & Sons, Inc. (1971), pages 32–36). The carboxylic acids are converted to the esters or amides by the conventional methods for forming esters or amides, for example via the acid chlorides or mixed anhydrides. For esterification with alcohols which still contain secondary amino groups, salts of the amino-alcohols are used.

In process (d), the compounds VI are reduced by known methods. Reducing agents which can be used are complex metal hydrides, for example sodium borohydride or lithium aluminum hydride, and solvents which can be used are methanol, ethanol, tetrahydrofuran or dimethoxyethane.

Process (e) also comprises a method which is known in principle and according to which compounds of the formula VII are converted to a compound, according to the invention, of the formula I which contains a formyl group as $R_2$. In addition to the carboxyl group itself, it is also possible to use, for example, esters, acid chlorides, acid anhydrides, acid amides or nitriles, as suitable carboxylic acid derivatives, and reducing agents which can be used are, for example, complex metal hydrides, such as lithium aluminum hydride or diisobutylaluminum hydride (compare "Compendium of Organic Synthetic Methods", publishers John Wiley & Sons, Inc. (1971), pages 132–137, 148–150, 152–153 and 166–168).

In process (f), the compounds VIII are reduced by known methods. Reducing agents which can be used are complex metal hydrides, such as sodium borohydride or lithium aluminum hydride, and solvents which can be used are methanol, ethanol, tetrahydrofuran or dimethoxyethane. The compounds VIII can be obtained from the compounds of the formula I which contain an aldehyde group as $R_2$, by reaction with an amine under acid catalysis. In this reaction, the water of reaction formed can preferably be separated off by means of a water separator.

In process (g), the compounds IX are reacted with an amine or alcohol in the presence of a hydrogen halide-binding agent. Hydrogen halide-binding agents which can be used are an excess of the amine itself, tertiary amines, such as triethylamine, pyridine or also potassium carbonate or the like and solvents which can be employed, if they are used for the reaction, are inert, anhydrous organic solvents, such as dioxane, 1,2-dimethoxyethane, diethylene glycol dimethyl ether, diethylene glycol dibutyl ether, benzene, toluene, xylene, chlorobenzene, N,N-dimethylformamide, dimethylsulfoxide or hexamethylphosphoric acid triamide. The reaction is in general carried out at a temperature between 20° and 180° C. and is preferably carried out at between 20° and 130° C. The compounds II, which are required for process (g), can be prepared by reacting the compounds V with halogenating agents, such as phosphorus trichloride or phosphorus tribromide, according to known methods.

In process (h), dehydrating agents which can be used are, for example, phosphorus pentoxide, phosphorus oxychloride and acetic anhydride. The reaction is in general carried out at a temperature between 50° and 150° C. and solvents which can be used are pyridine, benzene, toluene, N,N-dimethylformamide and the like.

According to process (i), secondary amino groups are alkylated with alkylating agents $Y-R_{16}$ by methods which are in themselves known.

According to process (j), substituents can be introduced by electrophilic substitution into the aromatic radical $R_3$. Methods of substitution include, in particular, halogenation, sulfonation or nitration, nitration being of particular interest. The procedure is to subject compounds of the formula I to the customary conditions for nitration (sulfuric acid, nitric acid, ice-cooling).

According to process (k), the substituents $R_4$ subsequently introduced on the radical $R_3$ or already present can now subsequently be changed so that further compounds of the formula I are formed, for example a nitro group can be changed by reduction, an amino group can be changed by alkylation or a methoxy group can be changed by ether-splitting. This may be illustrated by a few examples taken from the large number of possibilities. An amino compound is obtained by reduction of an aromatic nitro group, for example the corresponding 4-aminophenyl compound is obtained if $R_3$ represents the 4-nitrobenzoyl radical. This reduction is carried out in the customary manner, such as, for example, with Raney nickel in ethanol or with iron powder in hydrochloric acid solution. The acylation of an amino group is given as a further example. Thus, for example, if $R_3$ denotes the 4-aminophenyl radical, it can be converted under the customary conditions, such as, for example, with acetic anhydride in pyridine at low temperatures (0°–10° C.), to the 4-acetylaminophenyl radical. The diazotization of an aromatic amino group with subsequent reaction with a nucleophilic group is a further possibility for changing existing substituents. Thus, for example, if the radical $R_3$ denotes the 4-aminophenyl group it can be converted by means of nitrous acid (usually prepared from sodium nitrite and sulfuric acid) at low temperatures (0°–5° C.) to the corresponding diazonium salt, which then, for example, yields the 4-chlorophenyl radical, with hydrochloric acid in the presence of copper chloride, and the 4-hydroxyphenyl group, by boiling. The splitting of an alkoxy group to give the corresponding hydroxy compound is a further method for co verting the various substituents. Thus, for example, ether-splitting of a 7-methoxy compound ($R_4=OCH_3$) with, for example, hydrogen bromide in aqueous acetic acid at temperatures between 50° and 120° C. yields the corresponding 7-hydroxy compound. The oxidation of a methyl group to a carboxyl group or the reduction of an aldoxime group to an amino group may be mentioned as further examples.

The compounds according to the invention have valuable therapeutic properties. Thus, in addition to other pharmacological properties, they have an action on the central nervous system. They can prevent the spasms induced by an electric current or pentamethylenetetrazole and prolong thiopental or alcohol narcosis, but on the other hand intensify the convulsions induced by isonicotinic acid hydrazide and picrotoxin. By reason of all of these properties, the compounds according to the invention can be used as active ingredients in medicaments having an antidepressive, a sedative, tranquilizing, and antispasmodic action.

The dosage required to treat a human patient suffering from depressions depends on the nature and the extent of the depression. Generally, small dosages will be administered initially with gradual increase in dosage until the optimum dosage level is determined for the particular patient under treatment. It will generally be found that when the composition is administered orally, larger quantities of the active ingredient will be required to produce the same antidepressive effect as would be produced by the smaller quantity of the active compound which is administered parenterally. In general, dosages will be in the range from about 5 to 50 mg/kg per day if administered orally, whereas dosages of from 1 to 30 mg/kg per day are used for intravenous administration.

The new compounds can be used either on their own or as a mixture with physiologically acceptable adjuncts or carriers. For an oral use-form, the active compounds are mixed with the substances customarily used for this purpose and the mixture is brought, by means of conventional methods, into a suitable form for administration, such as tablets, dry-filled capsules, aqueous, alcoholic or oily suspensions or aqueous, alcoholic or oily solutions. Inert carriers which can be used are, for example, magnesium carbonate, lactose or maize starch. The formulation can be produced either in the form of dry granules or of moist granules. Oily carriers or solvents which can be used are, for example, especially vegetable and animal oils, such as, for example, sunflower oil or cod liver oil.

Intravenous application constitutes a particular use-form. For this purpose, the active compounds or their physiologically acceptable salts are brought into solution with the substances customarily used for this purpose. Such physiologically acceptable salts are, for example, formed with the following acids: hydrochloric acid, hydrobromic acid or hydroiodic acid, phosphoric acid, sulfuric acid, methylsulfuric acid, amidosulfonic acid, nitric acid, formic acid, acetic acid, propionic acid, succinic acid, tartaric acid, lactic acid, malonic acid, fumaric acid, oxalic acid, citric acid, malic acid, mucic acid, benzoic acid, salicylic acid, acetylglycine, embonic acid, naphthalene-1,5-disulfonic acid, ascorbic acid, phenylacetic acid, p-amino-salicylic acid, hydroxyethanesulfonic acid and benzenesulfonic acid, or synthetic resins which contain acid groups, for example those which have an ion exchange action. The solvents for the corresponding physiologically acceptable salts of the active compounds which can be used for intravenous administration are: water, physiological sodium chloride solutions or alcohol, such as, for example, ethanol, propanediol or glycerol, and in addition also sugar solutions, such as, for example, glucose or mannitol solutions, or a mixture of the various solvents mentioned.

EXAMPLE 1

3-N-Methylpiperazino-1-phenyl-isoquinoline-4-aldehyde

A mixture of 20 g of 3-chloro-1-phenyl-isoquinoline-4-aldehyde and 15 g of N-methylpiperazine is boiled in 200 ml of toluene under reflux for 4 hours. After cooling, the toluene solution is washed 4 times with, in each case, 200 ml of water, dried over magnesium sulfate and filtered and the solvent is removed in vacuo. The residue is ground with diisopropyl ether and 21.0 g of white crystals with a melting point of 152°–154° are filtered off. (Hydrochloride melting point 230°).

The isoquinoline-4-aldehydes substituted in the 3-position which are given as examples in Table 1 are prepared in the manner described above from the 3-chloroisoquinoline-4-aldehydes and the corresponding bases.

TABLE 1

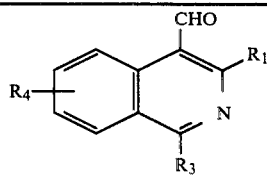

| Example | $R_1$ | $R_3$ | $R_4$ | Melting point °C., salt (melting point °C.) |
|---|---|---|---|---|
| 2 | −N\_/N−H | $C_6H_5$ | H | 147–149°, hydrochloride (218°) |
| 3 | −N\_/N−⟨pyridyl⟩ | $C_6H_5$ | H | 174–176° |

TABLE 1-continued

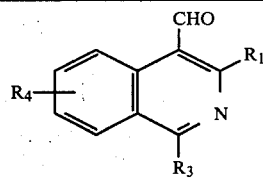

| Example | R₁ | R₃ | R₄ | Melting point °C., salt (melting point °C.) |
|---|---|---|---|---|
| 4 | -N(piperazine)N-CH₃ | 2,4-di-Cl—C₆H₃ | H | 166–168°, hydrochloride (231°) |
| 5 | -N(piperazine)N-CH₃ | 4-Cl—C₆H₄— | H | 182–184°, hydrochloride (230°) |
| 6 | -N(piperazine)N-CH₃ | C₆H₅ | 6,7-di-CH₃O | 158–160°, hydrochloride (214°) |
| 7 | —NH—CH₂—CH₂—N(C₂H₅)₂ | C₆H₅ | 6-Cl | oil, hydrochloride (212°) |
| 8 | -N(morpholine)O | C₆H₅ | H | hydrochloride (270°) |
| 9 | —NH—CH₂—CH₂—N(morpholine)O | C₆H₅ | H | dihydrochloride (>270°) |
| 10 | —NH—CH₂—CH₂—N(C₂H₅)₂ | 4-Cl—C₆H₄ | H | oil, hydrochloride (210°) |
| 11 | —N(CH₃)—CH₂—CH₂—N(CH₃)₂ | C₆H₅ | H | oil, hydrochloride (195°) |
| 12 | -N(piperazine)N-CH₃ | C₆H₅ | 6-Cl | 185–187°, hydrochloride (240°) |
| 13 | -N(piperazine)N-CH₃ | 2-F—C₆H₄ | H | 125–126°, hydrochloride (234°) |
| 14 | -N(piperazine)N-CH₃ | 2-CH₃—C₆H₄ | H | 143–146°, hydrochloride (235°) |
| 15 | -N(piperazine)N—CH₂—CH₂—C₆H₅ | C₆H₅ | H | 146–148°, hydrochloride (252°) |
| 16 | -N(piperazine)N—CH(CH₃)—C₆H₅ | C₆H₅ | H | 166–168°, hydrochloride (158°) |
| 17 | -N(piperidine)—NH—C(O)—C₆H₅ | C₆H₅ | H | 219–221° |
| 18 | -N(piperazine)N-CH₃ | 4-pyridyl | H | 181–182° |
| 19 | —NH—CH₂—CH₂—N(C₂H₅)₂ | C₆H₅ | H | 73–74° |

EXAMPLE 20

3-N-Carboethoxypiperazino-1-phenyl-isoquinoline-4-aldehyde 8.7 g of ethyl chloroformate are added dropwise to 9.55 g of 3-piperazino-1-phenyl-isoquinoline-4-aldehyde hydrochloride and 11.5 g of sodium carbonate in 200 ml of toluene, at room temperature, with stirring. The mixture is then boiled under reflux for 2 hours and cooled and the inorganic precipitate is filtered off. The filtrate is concentrated in vacuo and the residue is crystallized. 8.4 g of 3-N-carboethoxypiperazino-1-phenyl-isoquinoline-4-aldehyde with a melting point of 138°–140° C. are obtained.

EXAMPLE 21

3-N-[3-(4-Fluorobenzoyl)-propyl]-piperazino-1-phenyl-isoquinoline-4-aldehyde 9.5 g of 3-piperazino-1-phenyl-isoquinoline-4-aldehyde, 9.02 g of ω-chloro-4-fluoro-butyrophenone, 9.55 g of sodium carbonate and 0.2 g of potassium iodide are boiled under reflux in 200 ml of toluene for 7 days, with stirring. Working up as in Example 20 gives 15.8 g of a dark resin; with oxalic acid in ethyl acetate, this crystallizes as the oxalate with a melting point of 125° C.

EXAMPLE 22

3-N-Butylpiperazino-1-phenyl-isoquinoline-4-aldehyde

Oily 3-N-butylpiperazino-1-phenyl-isoquinoline-4-aldehyde, the hydrochloride of which melts at 202° C., is obtained analogously to the procedure of Example 21, using butyl bromide.

EXAMPLE 23

3-N-Ethylpiperazino-1-phenyl-isoquinoline-4-aldehyde

Yellowish crystals of 3-N-ethylpiperazino-1-phenyl-isoquinoline-4-aldehyde with a melting point of 136°–139° C. are obtained analogously to the procedure of Example 21, using ethyl iodide.

EXAMPLE 24

The compounds in Table 2 are prepared analogously to Example 21 from 3-piperazino-1-phenyl-isoquinoline-4-aldehydes and the corresponding alkyl halides.

TABLE 2

| R | $R_3$ | $R_4$ |
|---|---|---|
| $-CH_2-\text{◯}-O-CH_2-O$ (methylenedioxybenzyl) | $C_6H_5$ | H |
| $-CH_2-C\equiv CH$ | $C_6H_5$ | 6,7-di-$CH_3O$ |
| $-CH_2-CH=CH_2$ | 4-Cl-$C_6H_5$ | H |
| | $C_6H_5$ | 6-Cl |
| $-CH_2-\underset{\parallel}{C}(=O)-N\text{(piperidinyl)}$ | | |
| $-CH_2-CH_2-N(C_2H_5)_2$ | 4-pyridyl | H |

EXAMPLE 25

3-N-(2-Furoyl)-piperazino-1-phenyl-isoquinoline-4-aldehyde 6.44 g of furane-2-carboxylic acid chloride are added to 10.6 g of 3-piperazino-1-phenyl-isoquinoline-4-aldehyde hydrochloride in 300 ml of pyridine at 0° C. After stirring for 4 hours at room temperature, the solvent is removed in vacuo and the residue is crystallized from water. The product isolated has a melting point of 128° C.

EXAMPLE 26

The following compounds in Table 3 can be prepared analogously to Example 25.

TABLE 3

| R | $R_3$ | $R_4$ |
|---|---|---|
| $-CO-\text{◯}-O-CH_2-O$ (methylenedioxybenzoyl) | $C_6H_5$ | 6,7-di-$CH_3O$ |

TABLE 3-continued

[Reaction scheme: isoquinoline-CHO with piperazine-NH reacting with R-C(O)-Cl, giving two regioisomeric products with piperazine N-C(O)-R substituents]

| R | R₃ | R₄ |
|---|---|---|
| —CO—(3-pyridyl) | C₆H₅ | H |
| —CO—(4-pyridyl) | 4-Cl—C₆H₄ | H |
| —CO—(2-furyl) | 2,4-di-Cl—C₆H₃ | H |
| —CO—C₆H₃(OCH₃)₂ (3,4-dimethoxyphenyl) | C₆H₅ | H |
| —CO—C₆H₃(OCH₃)₂ (3,4-dimethoxyphenyl) | C₆H₅ | 6-Cl |
| —CO₂C₂H₅ | 4-pyridyl | H |

| R | R₃ | R₄ |
|---|---|---|
| —CO—C₆H₂(OCH₃)₃ (3,4,5-trimethoxyphenyl) | C₆H₅ | 7-CH₃O |

EXAMPLE 27

4-Hydroxymethyl-3-N-methylpiperazino-1-phenyl-isoquinoline 10 g of 3-N-methylpiperazino-1-phenyl-isoquinoline-4-aldehyde are suspended in 300 ml of methanol and 3.5 g of sodium borohydride are added in small portions at room temperature. The reaction mixture is stirred for a further 4 hours at room temperature, the solvent is removed in vacuo and the residue is stirred with 500 ml of water. 10.0 g of 4-hydroxymethyl-3-N-methyl-piperazino-1-phenylisoquinoline with a melting point of 153°–155° C. can be filtered off. Hydrochloride 225° C.

The examples listed in Table 4 are prepared correspondingly.

TABLE 4

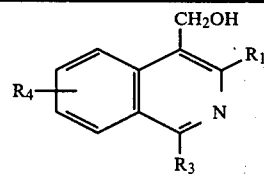

| Example | R₁ | R₃ | R₄ | Melting point °C., salt (melting point °C.) |
|---|---|---|---|---|
| 28 | —N(piperazinyl)—2-pyridyl | C₆H₅ | H | 179–181° C. |
| 29 | —N(piperazinyl)—N—CH₃ | 2,4-di-Cl—C₆H₅ | H | 109–116°, hydrochloride (238°) |
| 30 | —N(piperazinyl)—N—CH₂—CH₂—CH₂—CH(OH)—C₆H₄—F | C₆H₅ | H | 155–159° |
| 31 | —N(piperazinyl)—N—CH₃ | 4-Cl—C₆H₄ | H | 169–172°, hydrochloride (238°) |
| 32 | —N(piperazinyl)—N—CH₃ | C₆H₅ | 6,7-di-CH₃O | 164–170°, hydrochloride (230°) |

TABLE 4-continued

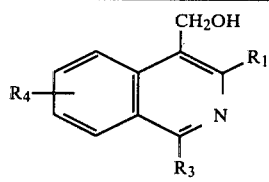

| Example | R₁ | R₃ | R₄ | Melting point °C., salt (melting point °C.) |
|---|---|---|---|---|
| 33 | —N(CH₂CH₂)₂N—CH₃ | C₆H₅ | 6-Cl | 202–205°, hydrochloride (254°) |
| 34 | —N(CH₂CH₂)₂N—CH₃ | C₆H₅ | 2-F | 140–143°, hydrochloride (229°) |
| 35 | —N(CH₂CH₂)₂N—CH₂—CH₂—C₆H₅ | C₆H₅ | H | 142–144°, hydrochloride (212°) |
| 36 | —N(CH₂CH₂)₂N—C₄H₉ | C₆H₅ | H | 102–104° |
| 37 | —N(CH₂CH₂)₂N—CH₃ | 3-Cl—C₆H₄ | H | 112–114° |
| 38 | —NH—CH₂—CH₂—N(C₂H₅)₂ | —C₆H₅ | H | 109–110° C. |
| 39 | —N(CH₂CH₂)₂N—CH₃ | 4-pyridyl | H | 210–215° C. |

EXAMPLE 40

4-Cyano-3-N-methylpiperazino-1-phenyl-isoquinoline 2.64 g of 3-chloro-4-cyano-1-phenylisoquinoline are boiled under reflux with 2.0 g of N-methylpiperazine in 60 ml of toluene for 6 hours. After cooling, the toluene phase is washed several times with water and dried and the solvent is removed in vacuo. The residue is recrystallized from methanol. 2.4 g with a melting point of 254°–256° C. Hydrochloride 256°–258° C.

The starting material can be prepared from 3-chloro-1-phenylisoquinoline-4-aldehyde as follows:

55.6 g of hydroxylamine hydrochloride are added to 53.6 g of 3-chloro-1-phenylisoquinoline-4-aldehyde in 150 ml of pyridine at 0° C. and after 2 hours at room temperature the solvent is removed in vacuo. The residue is partitioned between water and toluene. The toluene phase is dried and evaporated in a rotary evaporator. 43.2 g of the aldoxime with a melting point of 151°–154° C. are obtained.

91.4 g of phosphorus oxychloride are added to 67.3 g of the aldoxime in 700 ml of pyridine at 0° C. and the reaction mixture is then left to stand for 12 hours at room temperature. The reaction mixture is hydrolyzed with water and the crystalline precipitate is filtered off. After recrystallizing from ethanol, 47 g of 3-chloro-4-cyano-1-phenylisoquinoline with a melting point of 191°–193° C. are obtained.

EXAMPLE 41

4-Cyano-3-N-methylpiperazino-1-phenyl-isoquinoline 6.7 g of 3-N-methylpiperazino-1-phenyl-isoquinoline-4-aldoxime are treated with phosphorus oxychloride in pyridine as described above. After the customary working up, 5.1 g of 3-N-methylpiperazino-4-cyano-1-phenyl-isoquinoline with a melting point of 254°–256° C. are isolated.

The starting material is prepared as follows.

16.6 g of 3-N-methylpiperazino-1-phenyl-isoquinoline-4-aldehyde are treated in 150 ml of pyridine with 13.9 g of hydroxylamine hydrochloride, as described in Example 40. After the customary working up, 17.2 g of the aldoxime with a melting point of 234°–235° C. are isolated. Hydrochloride 235° C.

EXAMPLE 42

The compounds in Table 5 can be prepared analogously to Example 40 or 41.

TABLE 5

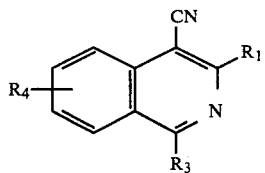

| R₁ | R₃ | R₄ |
|---|---|---|
| —N(piperazine)—C₄H₉ | C₆H₅ | H |
| —N(piperidine)—NH—C(=O)—C₆H₅ | C₆H₅ | 6,7-di-CH₃O |
| —N(morpholine) | 2-Cl—C₆H₄ | H |
| —N(azocane) | 2,4-di-Cl—C₆H₃ | H |
| —N(CH₃)—CH₂—CH₂—N(CH₃)CH₃ | C₆H₅ | H |
| —N(piperidine with H, OH at 4-position) | C₆H₅ | H |
| —N(piperazine)—N(2-OCH₃-C₆H₄) | C₆H₅ | 6-Cl |
| —N(2,6-dimethylmorpholine) | 4-Cl—C₆H₄ | H |
| —N(piperidine-CH₂OH) | C₆H₅ | H |
| —N(piperazine)—(2-pyridyl) | C₆H₅ | H |
| —N(piperazine)—(2-pyridyl) | 2-CH₃—C₆H₄ | H |

EXAMPLE 43

4-Aminomethyl-3-N-methylpiperazino-1-phenyl-isoquinoline 9.8 g of 3-N-methylpiperazino-1-phenyl-isoquinoline-4-aldoxime in 500 ml of methanol and 100 ml of 8 N methanolic ammonia solution are shaken with 10 g of Raney nickel in a hydrogen atmosphere at room temperature. After the theoretical amount of hydrogen has been taken up, the catalyst is filtered off and the solvent is removed in vacuo. The residue crystallizes from toluene and has a melting point of 122°–125° C. Hydrochloride 251° C.

EXAMPLE 44

1-Phenyl-3-piperazino-isoquinoline-4-carboxylic acid N-methyl-piperazide 12.06 g of 3-chloro-1-phenyl-isoquinoline-4-carboxylic acid N-methyl-piperazide in 50 ml of dioxane are boiled under reflux with 90 g of piperazine for 80 hours, with stirring. The reaction solution is poured into saturated sodium chloride solution and extracted with toluene. The toluene is removed in vacuo and the red-brown resin is crystallized as the hydrochloride. 14.7 g with a melting point of 280° C. are isolated.

The starting material employed can be prepared as follows.

53.5 g of 3-chloro-1-phenyl-isoquinoline-4-aldehyde are suspended in 1.5 l of acetone and 500 ml of phosphate buffer with a pH of 7. 40 g of potassium permanganate are introduced in portions in the course of 2 hours at 40° C. and the reaction mixture is stirred for a further 2 hours at this temperature. The excess potassium permanganate is destroyed with 10 g of sodium bisulfite and the solution is concentrated to 500 ml in a rotary evaporator and filtered. The pH of the filtrate is adjusted to 4 with concentrated hydrochloric acid and the solution is extracted thoroughly with ethyl acetate. After removing the solvent in vacuo, 41.1 g of 3-chloro-1-phenylisoquinoline-4-carboxylic acid with a melting point of 208° C. remain.

42.5 g of 3-chloro-1-phenyl-isoquinoline-4-carboxylic acid are boiled under reflux with 300 ml of thionyl chloride for 4 hours. The solution is evaporated in a rotary evaporator and the crude acid chloride is immediately subjected to further processing 11.3 g of the acid chloride in 75 ml of chloroform are added dropwise to 11.3 g of N-methylpiperazine in 100 ml of chloroform at room temperature. After 6 hours at room temperature, the solvent is removed and the residue is stirred with saturated sodium bicarbonate solution. 13.3 g of the N-methylpiperazide with a melting point of 164°–167° C. can be isolated. Hydrochloride 256° C.

The compounds in Table 6 can be prepared in accordance with Example 44.

TABLE 6

[Structure: isoquinoline with CO—R₂ at position 4, R¹ at position 3, phenyl at position 1]

| Example | R₁ | R₂ | Melting point °C., salt (melting point °C.) |
|---------|-----|-----|--------------------------------------------|
| 45 | —N(piperazino)N—CH₃ | —N(piperazino)N—CH₃ | 156–158°, dihydrochloride >290° |
| 46 | —N(piperazino)N—CH₂—CH₂—OH | —N(piperazino)N—CH₃ | oil, hydrochloride 273° |
| 47 | —N(piperazino)N—CH₂—CH₂—CH₂—C(O)—C₆H₄—F | —N(piperazino)N—CH₃ | oil, hydrochloride 140° |
| 48 | —N(piperazino)N—CH₃ | —NH—CH₂—CH₂—CH₂—N(CH₃)₂ | oil, di-hydrochloride >260° |
| 49 | —N(piperazino)N—CH₃ | —NH—CH₂—CH₂—N(morpholino) | oil, hydrochloride 170° |

EXAMPLE 50

3-(3-N-Methylpiperazino-1-phenyl-isoquinolin-4-yl)-acrylonitrile 4.43 g of cyanomethyldiethyl phosphate are added dropwise, at room temperature, to 0.6 g of sodium hydride in 75 ml of absolute dimethoxyethane, under nitrogen. After stirring for 45 minutes at room temperature, 8.3 g of 3-N-methylpiperazino-1-phenyl-isoquinoline-4-aldehyde dissolved in 100 ml of dimethoxyethane are added. The reaction mixture is left to stand for 12 hours at room temperature and is hydrolyzed with water, the solvent is removed and the residue is partitioned between toluene and water. 6.9 g of the acrylonitrile derivative with a melting point of 166°–168° are isolated from the toluene phase. Hydrochloride 245° C.

EXAMPLE 51

4-Ethoxy-methylene-3-N-ethylpiperazino-1-phenyl-isoquinoline 3 g of 4-hydroxymethyl-3-N-ethylpiperazino-1-phenylisoquinoline are dissolved in ethanol and the solution is heated with 10 ml of 0.2 N ethanolic hydrochloric acid on a water bath for 1 hour. The solvent is removed in vacuo and the crystals are stirred with acetone/ether. 2.3 g of the 4-ethoxymethylene compound remain in the form of the hydrochloride with a melting point of 186°.

EXAMPLE 52

4-Acetoxymethyl-3-N-methylpiperazino-1-phenyl-isoquinoline 1.1 g of acetyl chloride are added to 3.1 g of 4-hydroxymethylene-3-N-methylpiperazino-1-phenyl-isoquinoline in 30 ml of pyridine, at room temperature. After 4 hours at room temperature, the pyridine is removed in vacuo and the residue is partitioned between methylene chloride and water. 1.8 g with a melting point of 126°–128° C. are isolated from the methylene chloride phase.

EXAMPLE 53

The following substituted isoquinoline derivatives listed in Table 7 are prepared analogously to Example 52 from the corresponding 4-hydroxy-methylene derivatives and the corresponding acid chlorides.

TABLE 7

[Structure: isoquinoline with CH₂—O—CO—R at position 4, R₁ at position 3, R₃ at position 1, R₄ on benzene ring]

| R | R₁ | R₃ | R₄ |
|---|-----|-----|-----|
| 3,4-methylenedioxyphenyl-O-ethyl | —N(piperazino)N—CH₃ | C₆H₅ | H |
| " | " | 4-Cl—C₆H₄ | " |
| | | C₆H₅ | " |
| pyridyl (=N) | —N(piperazino)N—C₃H₇ | | |
| pyridyl | —N(piperazino)N—CH₃ | 4-Cl—C₆H₄ | 6,7-di-CH₃O |

TABLE 7-continued

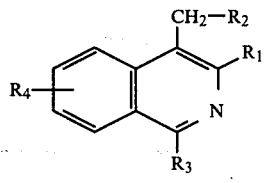

| R | $R_1$ | $R_3$ | $R_4$ |
|---|---|---|---|
| ![OCH3 phenyl] | " | 2-F—$C_6H_4$ | H |
| ![2,3,4-triOCH3 phenyl] | —N(morpholino) | $C_6H_5$ | " |
| ![4-NO2 phenyl] | —N(N-CH3 piperazino) | " | " |
| ![4-Cl phenyl] | —N(azepane) | " | " |

EXAMPLE 54

3-(3-N-Methylpiperazino-1-phenyl-isoquinolin-4-yl)-acrylaldehyde 2.13 g of 20% strength diisobutyl-aluminum hydride in toluene are added dropwise to 3.54 g of 3-(3-N-methylpiperazino-1-phenyl-isoquinon-4-yl)-acrylonitrile in 150 ml of toluene, at 0° C. under nitrogen blanketing gas. After stirring for 1 hour at 0° C., the reaction mixture is hydrolyzed with glacial acetic acid and the toluene phase is washed with water. After removing the solvent in vacuo, the oily residue is ground with ether and 2.8 g of product with a melting point of 130°–133° are filtered off.

EXAMPLE 55

4-(2-Diethylaminoethyl)-aminomethyl-3-N-methyl-piperazino-1-phenyl-isoquinoline 10 g of 3-N-methylpiperazino-1-phenyl-isoquinoline-4-aldehyde in 250 ml of methanol are boiled under reflux with diethylaminoethylamine for 10 hours. The methanol and the water of reaction are removed in vacuo and the residue is dissolved in 300 ml of fresh methanol. 6.86 g of sodium borohydride are added in portions, with ice-cooling, and the mixture is stirred for 12 hours at room temperature. The solvent is removed in vacuo and the residue is partitioned between ether and water. 14.5 g of product with a melting point of 95°–97° C. are isolated from the ether solution. Trimaleate: melting point 166°.

The compounds in Table 8 were prepared analogously to this example.

TABLE 8

| Example | $R_1$ | $R_2$ | $R_3$ | $R_4$ | Melting point, salt melting point |
|---|---|---|---|---|---|
| 56 | —N(N-CH3 piperazino) | —NH—$C_4H_9$ | $C_6H_5$ | H | oil, dimaleate 167° |
| 57 | —N(N-CH3 piperazino) | —NH—$CH_2$—$CH_2$—$CH_2$—N(CH3)(CH3) | " | " | 74–76°, trimaleate 158° |
| 58 | —N(N-H piperazino) | " | " | " | oil, trihydrochloride 166° |
| 59 | —N(N-$CO_2C_2H_5$ piperazino) | " | " | " | oil, dimaleate 154° |
| 60 | —N(piperidine-NH-C(O)-phenyl) | " | " | " | amorphous, dimaleate 123° |
| 61 | —N(N-C(O)-furyl piperazino) | " | " | " | oil, maleate 132° |

TABLE 8-continued

[Structure: isoquinoline core with CH₂—R₂ at 4-position, R₁ at 3-position, R₃ at 1-position, R₄ substituent on benzo ring]

| Example | R₁ | R₂ | R₃ | R₄ | Melting point, salt melting point |
|---|---|---|---|---|---|
| 62 | —N(CH₂CH₂)₂N—CH₃ | " | 2-F—C₆H₄ | " | 95–96°, trimaleate 143° |
| 63 | —N(CH₂CH₂)₂N—CH₃ | " | C₆H₅ | 6-Cl | oil, trimaleate 173° |
| 64 | —N(CH₂CH₂)₂N—CH₃ | " | 2-CH₃—C₆H₄ | H | oil, trioxalate 145° |

EXAMPLE 65

3-N-Methylpiperazino-4-(N-(2-methoxyphenyl)-piperazinomethyl)-1-phenyl-isoquinoline 4.81 g of 4-hydroxymethyl-3-(N-methylpiperazino)-1-phenyl-isoquinoline in 200 ml of toluene are stirred with 3.1 g of phosphorus pentachloride for 3 hours at room temperature. The solvent and the phosphorus oxychloride are removed in vacuo. The residue is then taken up in toluene and the solution is boiled under reflux with 7.15 g of 1-(o-methoxyphenyl)-piperazine for 4 hours. The toluene solution is then washed with water and concentrated. The resin which remains is converted to 3.4 g of the crystalline dihydrochloride with a melting point of >290°.

EXAMPLE 66

The following substituted isoquinoline derivatives listed in Table 9 are prepared in accordance with Example 51 or Example 65 from the 4-hydroxymethyl derivatives and the corresponding halogen compounds.

TABLE 9

[Structure: isoquinoline with CH₂—O—R at 4-position, R¹ at 3-position, R₃ at 1-position, R₄ substituent]

| R | R₁ | R₃ | R₄ |
|---|---|---|---|
| —CH₂—CH₂—N(C₂H₅)₂ | —N(CH₂CH₂)₂N—CH₃ | C₆H₅ | H |
| —CH₂—CH₂—CH₂—N(CH₃)₂ | —N(CH₂CH₂)₂N—CH₃ | 4-Cl—C₆H₄ | H |
| —CH₂—CH₂—N(morpholino) | —N(CH₂CH₂)₂N—CH₃ | C₆H₅ | 6,7-di-CH₃O |
| —CH₂—CH₂—N(pyrrolidino) | —N(CH₂CH₂)₂N—C₄H₉ | C₆H₅ | 6-Cl |
| —CH₂—CH(OH)—CH₂—N(piperazinyl-2-pyridyl) | —N(CH₂CH₂)₂N—CH₃ | C₆H₅ | H |
| —CH₂—CH(OH)—CH₂—NH—CH(CH₃)₂ | —N(CH₂CH₂)₂N—CH₃ | 2,4-di-Cl—C₆H₃ | H |
| —CH₂—CH₂—N(piperidino) | —N(CH₂CH₂)₂N—CH₃ | 2-F—C₆H₄ | H |

TABLE 9-continued

[Structure: isoquinoline with CH₂—O—R at position 4, R¹ at position 3, R₃ at position 1, R₄ substituent on benzene ring]

| R | R₁ | R₃ | R₄ |
|---|---|---|---|
| —CH₂—CH₂—N(C₂H₅)₂ | —N(piperazine)N—CH₃ | 4-pyridyl | H |
| —CH₂—CH₂—N(morpholino) | —N(piperazine)N—(2-pyridyl) | C₆H₅ | H |
| —CH₂—CH₂—NH—CH(CH₃)₂ | —N(piperazine)N—CH₃ | 2-CH₃—C₆H₄ | H |
| —CH₂—CH₂—NH—CH(CH₃)₂ | —N(piperazine)N—CH₃ | C₆H₅ | 6-Cl |
| —CH₂—CH₂—N(C₂H₅)₂ | —N(morpholino) | 4-Cl—C₆H₄ | H |
| —N(piperazine)N—CH₃ | —N(piperazine)N—CH₃ | C₆H₅ | H |
| —N(piperazine)N—CH₃ | —N(piperidine)—NH—CH₂—C₆H₅ | C₆H₅ | H |
| —N(piperazine)N—CH₃ | —N(piperazine)N—(2-pyridyl) | C₆H₅ | H |
| —N(piperazine)N—C₂H₅ | —N(CH₃)(CH₂—CH₂—N(CH₃)₂) | C₆H₅ | H |
| —N(piperazine)N—CH₃ | —N(piperazine)N—CH₃ | C₆H₅ | 6,7-di-CH₃O |
| —N(piperazine)N—CH₃ | —N(piperidine) | 4-pyridyl | H |
| —N(piperazine)N—CH₃ | —N(morpholino) | 4-Cl—C₆H₄ | H |

EXAMPLE 67:

3-N-(2-Pyridylpiperazino)-1-phenyl-isoquinoline-4-aldehyde

A mixture of 7.88 g of 4-hydroxymethyl-3-N-(2-pyridyl-piperazino)-1-phenyl-isoquinoline in 150 ml of chloroform is stirred with 4 g of activated manganese dioxide at room temperature for 6 hours. After filtering, the chloroform phase is washed with saturated sodium chloride solution and the solvent is removed in vacuo. The resinous residue is recrystallized from ethyl acetate and 4.2 g of product with a melting point of 170°–171° C. are thus isolated.

We claim:
1. An isoquinoline compound of the formula I

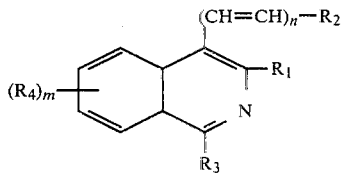

in which
m is one or two, n is zero or one,
$R_1$ is an amino group of the formula

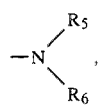

in which $R_5$ and $R_6$ are identical or different and are hydrogen or an alkyl radical with 1 to 8 carbon atoms, substituted alkyl radicals of 1 to 8 carbon atoms substituted by hydroxyl, $C_1$-$C_4$-alkoxy or an amino group of the formula

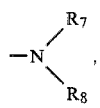

in which $R_7$ and $R_8$ are identical or different and represent hydrogen or a straight-chain or branched alkyl radical with 1 to 6 carbon atoms, or together with the nitrogen atom represent a heterocyclic ring with up to 7 carbon atoms, and wherein the alkyl radicals $R_5$ and $R_6$, when taken together with the nitrogen atom, define a 5-membered to 8-membered ring, and a substituted heterocyclic ring thereof on one of the carbon atoms with the substituents being a $C_1$-$C_6$-alkyl, $C_1$-$C_4$-alkoxy, hydroxyl, carboxyl or $C_1$-$C_4$-alkoxycarbonyl group, and in said ring one of said carbon atoms may further be replaced by an oxygen, sulfur, a nitrogen atom with a hydrogen atom thereon, or wherein the hydrogen atom on the nitrogen is replaced with a thienyl, furyl, pyridyl, or formyl group, a $C_3$-$C_8$-alkenyloxycarbonyl or $C_3$-$C_8$-alkynloxycarbonyl group, a $C_1$-$C_6$-alkoxy carbonyl group and substituted alkoxy carbonyl group substituted by hydroxy or $C_1$-$C_4$-alkoxy groups or a phenyl radical, or a substituted phenyl radical, wherein said phenyl may be substituted by up to three $C_1$-$C_4$-alkyl, $C_1$-$C_4$-alkoxy, mehtylenedioxy, hydroxyl, nitro or amino groups or halogen;

$R_2$ denotes a carboxyl, cyano, formyl or hydroxymethyl group, an alkoxymethyl group with 1 to 6 carbon atoms, an aminoalkyl group of the formula

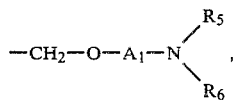

in which $A_1$ represents a straight-chain or branched $C_2$-$C_6$-alkylene group, which may be substituted by hydroxyl or $C_1$-$C_4$-alkoxy groups, and in which $R_5$ and $R_6$ are as defined above, an acyloxymethyl group of the formula —$CH_2$—O—CO—$R_{10}$, in which $R_{10}$ is a $C_1$-$C_6$-alkyl radical or a phenyl radical wherein said phenyl radicals may be substituted as defined above, an aminomethyl group of the formula

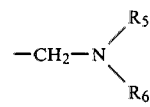

in which $R_5$ and $R_6$ are as defined above, a carboxamide group of the formula

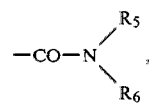

in which $R_5$ and $R_6$ are as defined above, or a carboxylic acid ester group of the formula

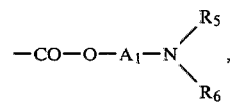

in which $A_1$, $R_5$ and $R_6$ are as defined above;

$R_3$ denotes a phenyl radical or a substituted phenyl group, monosubstituted or disubstituted with halogen, hydroxyl, nitro, amino or a substituted amino group with two to eighteen carbon atoms, a substituted amino group wherein the same is substituted by one or two aliphatic, cycloaliphatic or aromatic hydrocarbon radicals and in which the nitrogen atom may be incorporated in a heterocyclic ring, or an acylamino, alkyl or alkoxy group, each with one to six carbon atoms, a benzyloxy group of a trifluoromethyl group, or wherein $R_3$ denotes a pyridyl or thienyl radical; and $R_4$ denotes hydrogen, halogen, hydroxyl, an alkyl or alkoxy group with one to six carbon atoms, or a nitro, amino, benzyloxy or methylenedioxy or ethylenedioxy group and;

a physiologically acceptable salt thereof.

2. An isoquinoline as defined in claim 1, or a physiologically acceptable salt thereof, in which m is 1, n is 0, $R_1$ is piperazino or N-methylpiperazino, $R_2$ is formyl, hydroxymethyl or cyano, $R_3$ is phenyl, fluorophenyl or methylphenyl and $R_4$ is hydrogen.

3. The compound in claim 1 which is 3-N-methyl-piperazino-1-phenyl-isoquinoline-4-aldehyde.

4. The compound of claim 1 which is 3-N-methyl-piperazino-1-(2-fluorophenyl)-isoquinoline-4-aldehyde.

5. The compound of claim 1 which is 3-N-[3-(4-fluorobenzoyl)-propyl]-piperazino-1-phenyl-isoquinoline-4-aldehyde.

6. The compound of claim 1 which is 4-hydroxymethyl-3-N-methylpiperazino-1-phenyl-isoquinoline.

7. The compound of claim 1 which is 4-cyano-3-N-methylpiperazino-1-phenyl-isoquinoline.

8. The compound of claim 1 which is 3-N-methyl-piperazino-1-phenyl-isoquinoline-4-(3-dimethylaminopropyl) amide.

9. The compound of claim 1 which is 4-(2-diethylaminoethyl)-aminomethyl-3-N-methyl-piperazino-1-phenyl-isoquinoline.

10. The compound of claim 1 which is 3-piperazino-1-phenyl-isoquinoline-4-aldehyde.

11. The compound of claim 1 which is 3-N-methyl-piperazino-1-(2-methylphenyl)-isoquinoline-4-aldehyde.

12. An antidepressant composition which comprise an effective amount of a compound defined in claim 1 and a physiologically acceptable carrier therefor.

13. A method of treating a human patient having depressions which comprises oral administration of an effective dosage of from about 5 to 50 mg/kg per day of a compound as defined in claim 1.

14. A method of treating a human patient having depressions which comprises intravenous administration to said patient of an effective dosage of from about 1 to 30 mg/kg per day of a compound as claimed in claim 1.

* * * * *